United States Patent [19]

Street

[11] Patent Number: 5,334,174
[45] Date of Patent: Aug. 2, 1994

[54] PERSONAL WASTE DISPOSAL GARMENTS

[75] Inventor: Norman A. Street, Newark, Del.

[73] Assignee: W. L. Gore & Associates, Inc., Newark, Del.

[21] Appl. No.: 48,012

[22] Filed: Jan. 25, 1993

Related U.S. Application Data

[63] Continuation of Ser. No. 803,288, Oct. 23, 1991, abandoned.

[51] Int. Cl.$^5$ .................... A62B 17/00; A61M 1/00
[52] U.S. Cl. ..................... 604/313; 604/315; 2/227; 2/2.11
[58] Field of Search .......... 604/289, 313, 315, 319, 604/322, 323, 324, 326; 2/2.1 A, DIG. 3, 69, 227

[56] References Cited

U.S. PATENT DOCUMENTS

| | | | |
|---|---|---|---|
| 3,034,131 | 5/1962 | Lent | 2/2.1 A |
| 3,626,941 | 12/1971 | Webb . | |
| 4,023,223 | 5/1977 | Anderson et al. | 2/2.1 A X |
| 4,194,041 | 3/1980 | Gore . | |
| 4,200,102 | 4/1980 | Duhamel et al. . | |
| 4,230,114 | 10/1980 | Feather | 2/227 X |
| 4,443,511 | 4/1984 | Worden et al. . | |
| 4,455,683 | 6/1984 | Moretti | 2/2.1 A X |
| 4,583,246 | 4/1986 | Griswold | 2/2.1 A |
| 4,713,066 | 12/1987 | Komis . | |
| 4,820,291 | 4/1989 | Terauchi et al. | 4/454 |
| 4,923,741 | 5/1990 | Kosmo et al. | 428/252 |
| 4,932,078 | 6/1990 | Jones et al. . | |

FOREIGN PATENT DOCUMENTS 2590480   5/1987   France .

Primary Examiner—Randall L. Green
Assistant Examiner—Mary Beth O. Jones
Attorney, Agent, or Firm—Dena Meyer Weker

[57] ABSTRACT

A vacuum powered personal waste garment apparatus comprising a waterproof and breathable garment having thigh bands and a waistband that are snug when worn on a patient.

A first hose attached to a warm water supply on one end and the garment through a cuff at the other end to provide a fresh supply of water to the garment.

A second hose attached to a wet-dry vacuum cleaner on one end and the garment through a cuff at the other end wherein the vacuum cleaner creates a vacuum within the garment so that any liquid or solid waste within the garment flows into the second hose to the vacuum cleaner.

6 Claims, 1 Drawing Sheet

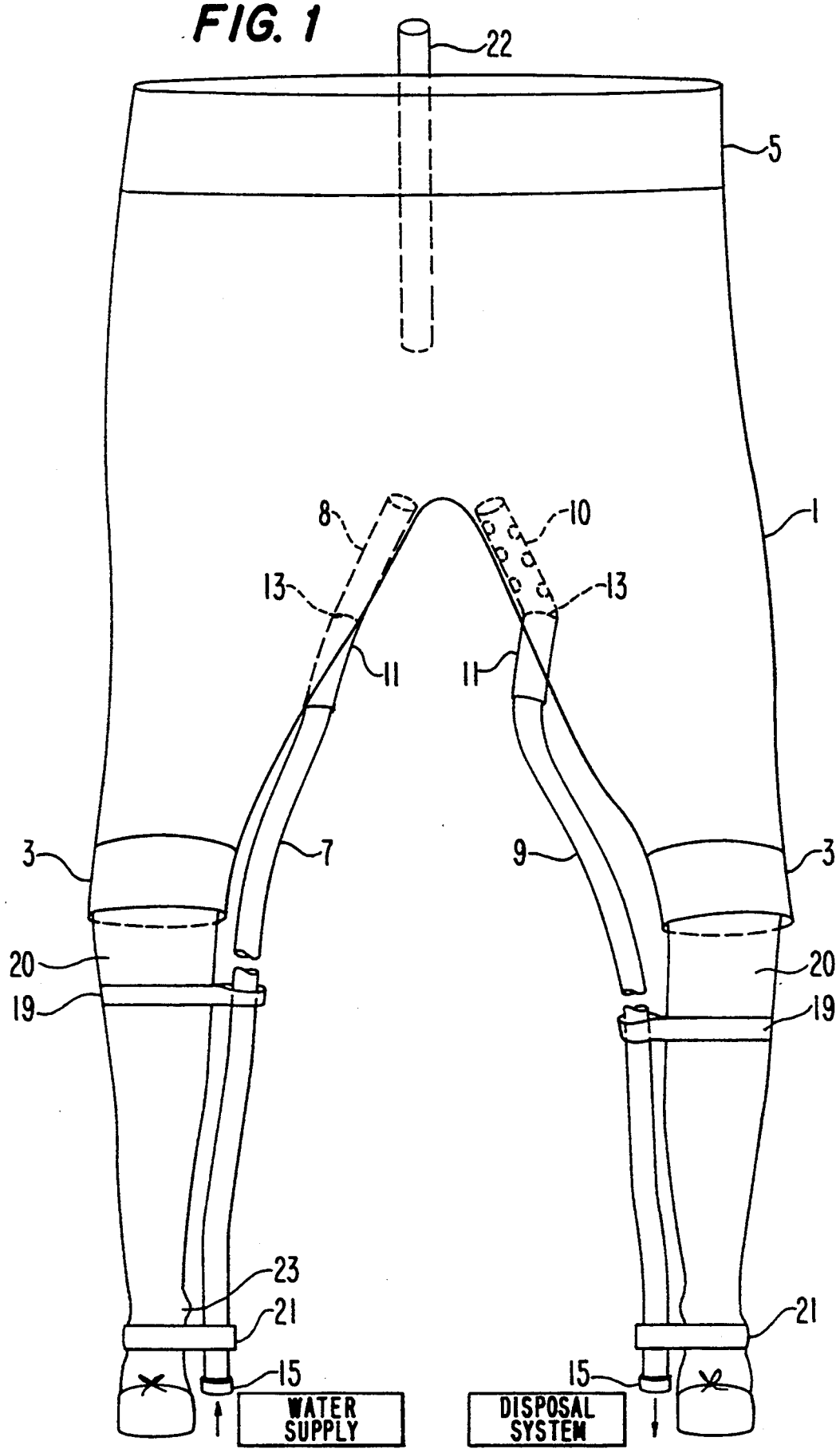

PERSONAL WASTE DISPOSAL GARMENTS

This application is a continuation of application Ser. No. 07/803,288 filed Oct. 23, 1991, now abandoned.

FIELD OF THE INVENTION

This invention relates to personal waste disposal garments in which human waste materials are flushed away from the wearer and requires the use of waterproof, breathable, snugly fit garments, preferably pants, equipped with supply and discharge hoses.

BACKGROUND OF THE INVENTION

Removal of human waste is a very personal matter. Two situations where improved removal systems are needed and where until now have received little or no attention are removal of human waste in zero gravity environments (e.g. astronauts in outer space) and human incontinence.

Astronauts in outer space have a particularly difficult time. They have found that the limitations associated with disposable diapers are very inhibiting when used with space suits particularly when used for extended periods of time.

Human incontinence problems are also very extensive, ranging from infants to elderly people or handicapped individuals. Human incontinence affects people of both sexes. Traditionally, removal of human wastes from incontinent people has been by passive means, namely by the use of diapers which require constant changing or the use of bed pans.

Use of diapers requires frequent servicing involving removal of contaminated diapers, cleaning the patient's body to remove any remaining fecal matter or urine and replacement of diapers. Diapers must be removed quite often to minimize bed sores and decubitus ulcers arising from residual ammonia of urine. Disposal of diapers also pose to present a larger environmental problem in future years as landfills become more scarce. The problems are compounded in a zero gravity environment.

There is a need for a system that provides a means of removing human waste materials on demand.

SUMMARY OF THE INVENTION

The present invention relates to a system in which human waste materials are removed on demand comprising a waterproof, breathable garment, snugly fit over the middle trunk of the patient, a vacuum pipe connected to the inside of the garment that removes solid and liquid waste materials to a disposal system such as a wet-dry vacuum and a second hose attached to a water supply that supplies warm water into the garment for flushing. Preferably the garment is a pair of short close fitting pants with waist and leg closures.

The present invention operates in an analogous manner to both a water closet and a bidet in which the waste products are captured and flushed away. Unlike the water closet however, the present invention operates independent of gravitational forces to remove waste but rather relies on the vacuum effect created within the pants. The vacuum causes the pants to collapse and close up any space between the fabric and the body of the wearer, behaving like a diaphragm pump in squeezing any fluid materials towards the discharge vacuum hose. This is particularly useful for astronauts in outer space who operate in weight loss environments.

A fresh water supply that may optionally contain additives such as bactericides, mild detergents and deodorizers is also used in conjunction with the exhaust vacuum system. The fresh water supply hose is arranged to be adjacent to the exhaust hose and penetrate the leg portion of the pant. Preferably it is mounted at the front of the vacuum hose. The purpose of this water flush is analogous firstly to the water closet in that it assists in the conveyance of the waste materials away from the patient's body and towards the vacuum system. Secondly the water flush supply also serves as a bidet in that the water cleanses the patient's skin and body within the pant area. The system is very efficient in the removal of liquid bodily waste however the efficiency of removal of solid waste varies and depends on the ease at which the solid waste is broken down and washed away by the water flow.

The vacuum system includes an entrance port within the pant area that is fitted with a cage of corrosion resistant material that is comfortable to the patient such as polypropylene that is capable of withstanding vacuum pressures and yet is pliable so that it will mold to the patient's contour. The purpose of the cage over the exit pipe is to prevent blockage. The vacuum pressure should be sufficient to cause the garment to collapse against the skin.

The water flush for the removal of urine is not essential since the urine will flow readily through the system under vacuum. Further, by employing breathable, waterproof fabric, the residual liquid dries rapidly whether it be urine or water. A water flow is preferable but may not be essential in a portable arrangement.

The exhaust pipe can be of any dimension so long as it is not cumbersome to the patient.

Preferably the system should be used with the patient in the supine position but is also suitable for sitting and standing. The system may be portable so long as both the water supply system, and the disposal system can be mobile. This system is more convenient for the removal of urine.

BRIEF DESCRIPTION OF THE DRAWING

FIG. 1 is a plan exploded view of the garment according to the present invention.

DETAILED DESCRIPTION OF THE EMBODIMENTS

The invention is best understood by reference to the figures. FIG. 1 shows a front view of the vacuum powered incontinent garment system in which pants 1 are used.

The pants 1 must be waterproof and breathable so as to provide comfort to the wearer in the course of normal activity. While any waterproof breathable materials are suitable for the garment, a preferred material comprises a hydrophobic and hydrophilic composite such as that described in U.S. Pat. No. 4,194,041. The material used for the garment must also be capable of forming a watertight seal and must be capable of being seam sealed. One type material satisfying these needs include a GORE-TEX ® fabric, an expanded polytetrafluoroethylene fabric commercially available from W. L. Gore & Associates, Inc., backed with a polyester tricot knit. A garment was made using this material in which all seams were seam-sealed to ensure that the system was entirely leakproof. Garment thigh bands 3 and waist band 5 should be made of an elastic material and also should be waterproof and breathable. A preferable material for the thigh bands and waist band is GORE-TEX fabric laminated to a stretch preferably 5.6 ounce knitted nylon Lycra ® fabric of which the material is commercially available from E. I. DuPont de Nemours, Inc. The elastic bands enable the garment to provide an enclosed system. The liquid seals obtained at the waist and thighs are of extreme importance since leaks at these points nullify the other membrane capabilities. Although GORE-TEX fabric is the preferred material, any other fabric that has a high moisture vapor transmission rate (at least 500 grams/meter$^2$/day) and that preferably remains waterproof even in the presence of human oils is suitable.

In the preferred embodiment, all seams are sewn with a multifilament polyester thread and seam sealing normally takes place on the exterior side of the garment.

The stretch bands 3 and 5 are attached to the main body of the garment by the filament polyester thread. The stretch bands should have the property of stretching at a ratio of about 1.5 to 1 which covers the thigh bands and waistband to be snug against the patient without causing discomfort. The bands should be about two inches in width, the area of which is in contact with the patient's skin. Narrower and wider bands however are acceptable.

Alternatively, a garment made entirely out of a stretchable material is also suitable for the system. In this case the material is also waterproof and breathable and the stretchiness provides additional support. Material suitable for this embodiment includes the GORE-TEX ® fabric laminated to a stretchy material similar to that used for the elastic cuffs and waist band. Stretching GORE-TEX fabric made in accordance with U.S. Pat. No. 4,443,511 is also suitable.

The water inlet hose Z, as designated by the upward arrow and outlet hose 9, as designated by the downward arrow are made of flexible waterproof tubing such as polyvinyl chloride (PVC). They typically approach the garment by being tied to one leg of the wearer. The ends of these hoses penetrate the pant at the point where there is a further stretch cuff 11 of small dimensions to accept the hoses and create a watertight seal. The stretch cuff 11 is preferably made of the same material as the stretch waist band and thigh bands. Similarly, all seams in the cuff and made to attach the cuff to the body of the garment are seam-sealed.

The water inlet hose may be three quarters of an inch outside diameter by five eighths of an inch inside diameter which penetrates about four inches, into the pants is shown as regions 8 and 10. The inlet hose 7 delivers water while the outlet hose 9 extracts fluid material from its intake end and from a plurality of holes preferably about twenty holes penetrating the last four inches of this hose. Alternatively a polypropylene cage may be used. Each hose is fitted with a retaining collar 13. These retaining collars 13 prevent the hoses 7 or 9 from slipping out of the stretch cuff 11. Both hoses are long enough to reach the knee or ankle area of the user.

At the lower end of each hose, there is a connector screw coupling 15 for attachment of a water supply to the inlet tube as designated by the upward arrow and a vacuum take-off to a wet and dry receiver from the exit tube 9 as designated by the downward arrow.

Anchor bands 19 made of stretch material attach the hoses to the user above or below the Knee 10. Ankle anchor bands 21 may similarly be attached to the user above or below the ankle.

The system may run continuously however preferably the patient is able to control the operation by periodic switching of controls. When the system is activated, a flow of warm water from a reservoir starts out as a flush to partially fill the pant cavity before the exhaust vacuum is activated to do the extraction. The warm water may optionally contain a mild bactericide, mild detergent and/or a pH neutralizer. Activation can be triggered manually or by a probe sensor.

The vacuum is then activated so that the discharge flows away to a wet and dry vacuum which has a pre-wetting stage with a sanitizing agent typically found in mobile toilets to minimize offensive odors. Alternatively a positive displacement such as a peristaltic pump may be used to discharge the waste directly to a lavatory pan.

For comfort, a drying period should ensue. This can be achieved by relying on the permeability and breathability of the expanded PTFE fabric or accelerated by continuing to run the vacuum exhaust while at the same time allowing airflow to increase by breaking the seal of the garment at the waistband.

Should the wearer feel discomfort, the cycle of back flush with warm water and vacuum extract can be repeated as many times as he likes. For complete drying, it is important to stop the warm water supply and continue operation of the pump as mentioned above. The vacuum within the pant region may be easily released by lifting the waistband and inserting a short tube 22 preferably in line with the wearer's backbone. The tube 22 may be used to hold the waistband away from the body and permit the passage of air for the drying out process. The tube may be made of rubber or plastic material that is warm to touch, but must have sufficient resilience to hold the waistband away and not cause discomfort to the patient.

It has been found that about ten minutes is sufficient under normal atmospheric conditions to evacuate the liquid waste and water from the pants; the drying time is dependent on temperature, humidity and volume of air swept through the system after entrance from the tube at the waistband.

What is claimed;

1. A personal waste disposal undergarment apparatus comprising:
   (a) a waterproof and breathable undergarment having cuffs and a waist band that are watertight when worn on a patient and wherein said undergarment is collapsible on the patient;
   (b) a first hose attached to a warm water supply on one end and to the inside of the undergarment at the other end to provide a fresh supply of water into the undergarment; and
   (c) a second hose attached to a disposal system on one end and to the undergarment at the other end wherein a waste stream escapes by vacuum to a disposal system.

2. A personal waste disposal undergarment apparatus of claim 1 wherein the undergarment is a pair of pants on said waistband comprises elastic and wherein said cuffs comprise elastic thigh bands, and said undergarment further comprising elastic cuffs at the locations where the first and second hoses attach to the undergarment.

3. A personal waste disposal undergarment apparatus of claim 1 wherein the undergarment is made of expanded polytetrafluoroethylene laminated to fabric.

4. A personal waste disposal undergarment apparatus of claim 1 wherein the warm water supply also contains additives from the group consisting of bactericides and mild detergents.

5. A personal waste disposal undergarment apparatus of claim 1 wherein the undergarment is disposable.

6. A personal waste disposal undergarment of claim 1 wherein the undergarment is stretchy and made of a laminate of expanded polytetrafluoroethylene and a stretch fabric.

* * * * *